US009029385B2

(12) United States Patent
Raghu et al.

(10) Patent No.: US 9,029,385 B2
(45) Date of Patent: May 12, 2015

(54) COMPOSITIONS AND METHODS FOR TREATING FIBROPROLIFERATIVE DISORDERS

(76) Inventors: Ganesh Raghu, Edmonds, WA (US); Douglas Harry Unwin, North Vancouver (CA); Lola Maksumova, Delta (CA)

( * ) Notice: Subject to any disclaimer, the term of this patent is extended or adjusted under 35 U.S.C. 154(b) by 419 days.

(21) Appl. No.: 12/739,934

(22) PCT Filed: Oct. 23, 2008

(86) PCT No.: PCT/CA2008/001880
§ 371 (c)(1),
(2), (4) Date: Sep. 24, 2010

(87) PCT Pub. No.: WO2009/052630
PCT Pub. Date: Apr. 30, 2009

(65) Prior Publication Data
US 2011/0009431 A1 Jan. 13, 2011

Related U.S. Application Data

(60) Provisional application No. 60/983,026, filed on Oct. 26, 2007.

(51) Int. Cl.
*A61K 31/522* (2006.01)
*A61K 31/198* (2006.01)
*A61P 1/16* (2006.01)
*A61P 9/00* (2006.01)
*A61K 45/06* (2006.01)

(52) U.S. Cl.
CPC .............. *A61K 45/06* (2013.01); *A61K 31/198* (2013.01); *A61K 31/522* (2013.01)

(58) Field of Classification Search
CPC ........................... A61K 31/522; A61K 31/198
USPC .............. 514/263, 562, 183, 263.36, 263.31
See application file for complete search history.

(56) References Cited

U.S. PATENT DOCUMENTS

| | | | |
|---|---|---|---|
| 5,310,562 | A | 5/1994 | Margolin |
| 5,518,729 | A | 5/1996 | Margolin |
| 5,645,839 | A | 7/1997 | Chobanian |
| 5,716,632 | A | 2/1998 | Margolin |
| 5,985,592 | A | 11/1999 | Peterson |
| 6,025,151 | A | 2/2000 | Peterson |
| 6,139,847 | A | 10/2000 | Chobanian |
| 6,284,763 | B1 | 9/2001 | Adams |
| 6,294,350 | B1 | 9/2001 | Peterson |
| 6,331,543 | B1 | 12/2001 | Garvey |
| 2003/0216407 | A1 | 11/2003 | Butt |
| 2005/0085486 | A1 | 4/2005 | Gonzalez-Cadavid |

FOREIGN PATENT DOCUMENTS

| | | |
|---|---|---|
| EP | 1079852 B1 | 5/1999 |
| JP | 2003-055215 A | 2/2003 |
| WO | 9426249 A1 | 11/1994 |
| WO | 9741830 A1 | 11/1997 |
| WO | WO 01/32156 A2 | 5/2001 |
| WO | WO 01/89517 A2 | 11/2001 |
| WO | WO 20041037183 A2 | 5/2004 |
| WO | 2005046676 A1 | 5/2005 |
| WO | 2005053768 A1 | 6/2005 |

OTHER PUBLICATIONS

D. Schuppan et al.;Pentoxifylline downregulates profibrogenic cytokines and procollagen I expression in rat secondary biliary fibrosis; Accepted May 1, 2001;GUT: International Journal of Gastroenterology and Hepatology; 50(2);241-247.*
J. Bonner; Regulation of PDGF and its receptors in fibrotic diseases; Elsevier; Cytokine & Growth Factor Reviews; 15 (2004) 255-273.*
X. Li et al. ;Revascularization of ischemic tissues by PDGF-CC via effects on endothelial cells and their progenitors;Journal of Clinical Investigation; 115; 1; Jan. 2005; 118-127.*
S. Demir et al.; Pentoxifylline and N-acetylcysteine in hepatic ischemia/reperfusion injury; Elsevier; Clinica Chimica Acta; 275 (1998) 127-135 (accepted Apr. 8, 1998).*
Ischemia_Merriam_Webster_Medical_Dictionary.*
U.S. National Library of Medicine_ADAM_Apr. 2010.*
English Abstract for JP 2003-055215, published Feb. 26, 2003. Translation supplied by espacenet database.
International Search Report for Application No. PCT/CA2008/001880, filed Oct. 23, 2008, search report mailed Feb. 6, 2009, 3 pages.
Aboutwerat, A., et al., "Oxidant stress is a significant feature of primary biliary cirrhosis", Biochim Biophys Acta, 2003, 1637(2):142-150.
Amores-Sanchez, M.I. and M.A. Medina, "Glutamine, as a precursor of glutathione, and oxidative stress", Mol Genet Metab, 1999, 67(2):100-105.
Aruoma, A., et al., "The antioxidant action of N-acetylcysteine: its reaction with hydrogen peroxide, hydroxyl radical, superoxide, and hypochlorous acid", Free Radic Biol Med, 1989, 6(6):593-597.
Aviado, Domingo M. and Harold R. Dettelbach, "Pharmacology of Pentoxifylline a hemorheologic agent for the treatment of intermittent claudication", Angiology, 1984, 35(7):407-417.
Bridgeman, M.M., et al., "Cysteine and glutathione concentrations in plasma and bronchoalveolar lavage fluid after treatment with N-acetylcysteine", Thorax, 1991, 46(1):39-42.

(Continued)

*Primary Examiner* — Kendra D. Carter
*Assistant Examiner* — Jason A Deck
(74) *Attorney, Agent, or Firm* — Chernoff, Vilhauer, McClung & Stenzel, LLP

(57) ABSTRACT

The present invention relates, in general, to fibroproliferative disorders, and, in particular, to methods and compositions for treating fibroproliferative disorders by administering to a mammal in need of treatment pharmacologically effective doses of a phosphodiesterase inhibitor, such as pentoxifylline, and an anti-oxidant which is a precursor of glutathione, such as N-acetyl-cysteine, or their derivatives or metabolites.

18 Claims, 8 Drawing Sheets

(56) References Cited

OTHER PUBLICATIONS

Cantin, A.M., et al., "Normal alveolar epithelial lining fluid contains high levels of glutathione", J Appl Physiol, 1987, 63 (1):152-157.
Cantin, A.M., et al., "Oxidant-mediated epithelial cell injury in idiopathic pulmonary fibrosis", J Clin Invest, 1987, 79 (6):1665-1673.
Chen, Y.M., et al., "Pentoxifylline suppresses renal tumour necrosis factor-alpha and ameliorates experimental crescentic glomerulonephritis in rats", Nephrol Dial Transplant, 2004, 19(5):1106-1115.
Chol, M., et al., "Glutathione precursors replenish decreased glutathione pool in cystinotic cell lines", Biochem Biophys Res Commun, 2004, 324(1):231-235.
Cortijo, J., et al., "Attenuation by oral N-acetylcysteine of bleomycin-induced lung injury in rats", Eur Respir J, 2001, 17(6):1228-1235.
Davis, Patrick J., et al., "Microbial models of mammalian metabolism: Microbiol reduction and oxidation of pentoxifylline", Applied and Environmental Microbiology, 1984, 48(2):327-331.
Desmouliere, A., et al., "Effect of pentoxifylline on early proliferation and phenotypic modulation of fibrogenic cells in two rat models of liver fibrosis and on cultured hepatic stellate cells", J Hepatol, 1999, 30(4):621-631.
Duncan, Matthew R., et al., "Pentoxifylline, pentifylline, and interferons increase Type I and III procollagen mRNA levels in dermal fibroblasts: evidence for mediation by nuclear factor 1 down-regulation", Journal of Investigative Dermatology, 1995, 104:282-286.
Entzian, P., et al., "Comparative study on effects of pentoxifylline, prednisolone and colchicine in experimental alveolitis", Int J Immunopharmacol, 1998, 20(12):723-735.
Fang, C., et al., "Effects of pentoxifylline on peritoneal fibroblasts and silica-induced periotoneal fibrosis", Perit Dial Int, 2003, 23(3):228-236.
Fantin, M., et al., "Pentoxifylline and its major oxidative metabolites exhibit different pharmacological properties", Eur J Pharmacol, 2006, 535(1-3):301-309.
Hagiwara, S.I., et al., "Aerosolized administration of N-acetylcysteine attenuates lung fibrosis induced by bleomycin in mice", Am J Respir Crit Care Med, 2000, 162(1):225-231.
InterMune Investor Relations, InterMune (ticker:ITMN, exchange: NASDAQ Global Market (.O)) News Release—May 17, 2006, "InterMune Announces Presentation on Actimmune and Perfenidone at American Thoracic Society Conference", Accessed Apr. 9, 2007, <http://www.corporate-ir.net/ireye/ir_site.zhtml?ticker=ITMN&script_410&layout+6&ite . . . >.
Kawada, N. and K. Otogawa, "Role of oxidative stress and Kupffer cells in hepatic fibrosis", J Gastroenterol Hepatol, 2007, 22 Suppl 1:S85-S86.
Keays, R., et al., "Intravenous acetylcysteine in paracetamol induced fulminant hepatic failure: a prospective controlled trial", BMJ, 1991, 303(6809):1026-1029.
Kohyama, T., et al., "PDE4 inhibitors attenuate fibroblast chemotaxis and contraction of native collagen gels", Am J Respir Cell Mol Biol, 2002, 26(6):694-701. ama, T., et al., "PDE4 inhibitors attenuate fibroblast chemotaxis and contraction of native collagen gels", Am J Respir Cell Mol Biol, 2002, 26(6):694-701.
Kovanecz, I., et al., Chronic daily tadalafil prevents the corporal fibrosis and veno-occlusive dysfunction that occurs after cavernosal nerve resection, BJU International, 2007, 101:203-210.
Mata, M., et al., "Oral N-acetylcystine reduces bleomycin-induced lung damage and mucin Muc5ac expression in rats", Eur Respir J., 2003, 22(6):900-905.
Meister, A., "Glutathione metabolism and its selective modification", J Biol Chem, 1988, 263(33):17205-17208.
Meyer, A, et al., "The effect of oral N-acetylcysteine on lung glutathione levels in idiopathic pulmonary fibrosis", Eur Respir J, 1994, 7(3):431-436.
Moore, B.B. and C.M. Hogaboam, "Murine models of pulmonary fibrosis", Am J Physiol Lung Cell Mol Physiol, 2008, 294(2):L152-L160.
Moriyama, T., et al., "Oxidative stress in tubulointerstitial injury: therapeutic potential of antioxidants towards interstitial fibrosis", Nephrol Dial Transplant, 2000, 15 Suppl 6:47-49.
Muller, R. and F. Lehrach, "Haemorheology and cerebrovascular disease: multifunctional approach with pentoxifylline", Curr Med Res Opin, 1981, 7(4):253-263.
Ozes, O.N., et al., [Poster Board #B26] Pirfenidone inhibits transforming growth factor-beta-induced expression of b-JUN and prolongs tumor necrosis factor-alpha activation of c-JUN: implications for the treatment of idiopathic pulmonary fibrosis (publication p. A186), May 21, 2006.
Raetsch, C., et al., "Pentoxifylline downregulates profibrogenic cytokines and procollagen I expression in rat secondary biliary fibrosis", Gut, 2002, 50(2):241-247.
Rahman, I., et al., "Oxidant and antioxidant balance in the airways and airway disease", Eur J Pharmacol, 2006, 533(1-3):222-239.
Rawlins, J.M., et al., "Pentoxifylline inhibits mature burn scar fibroblasts in culture", Burns, 2006, 32(1):42-45.
Sadowska, A.M., et al., "Antioxidant and anti-inflammatory efficacy of NAC in the treatment of COPD: discordant in vitro and in vivo dose-effects: a review", Pul Pharmacol Ther, 2007, 20(1):9-22.
Serrano-Mollar, A., et al., "In vivo antioxidant treatment protects against bleomycin-induce lung damage in rats", Br J Pharmacol, 2003, 138(6):1037-1048.
Smilkstein, Martin J., et al., "Efficacy of oral-N-acetylcysteine in the treatment of acetaminophen overdose", The New England Journal Medicine, 1988, 319(24): 1557-1562.
Stutz, F., et al,. "Effects of pentoxifylline, pentifylline and gamma-interferon on proliferation, differentiation, and matrix synthesis of human renal fibroblasts", Nephrol Dial Transplant, 2000, 15(10):1535-1546.
Valente, E.G., et al., "L-arginine and phosphodiesterase (PDE) inhibitors counteract fibrosis in the Peyronie's fibrotic plaque and related fibroblast cultures", Nitric Oxide, 2003, 9(4):229-244.
Verma-Gandhu, M., et al., "Effects of fetuin, a TGFbeta antagonist and pentoxifylline, a cytokine antagonist on hepatic stellate cell function and fibrotic parameters in fibrosis", Eur J Pharmacol, 2007, 572(2-3):220-227.
Windmeier, C. and A.M. Gressner, "Effect of pentoxifylline on the fibrogenic functions of cultured rat liver fat-storing cells and myofibroblasts", Biochem Pharmacol, 1996, 51(5):577-584.
Windmeier, C. and A. M. Gressner, "Pharmacological aspects of pentoxifylline with emphasis on its inhibitory actions on hepatic fibrogenesis", Gen. Pharmac., 1997, 29(2):181-196.
Wynn, Thomas A., "Common and unique mechanisms regulate fibrosis in various fibroproliferative diseases", J Clin Invest, 2007, 117(3):524-529.
Xiong, L.J., et al., "Effects of pentoxidylline on the hepatic content of TGF-beta 1 and collagen in Schistosomiasis japonica mice with liver fibrosis", World J Gastroenterol, 2003, 9(1):152-154.
Peterson, T.C., et al., "In vitro effect of platelet-derived growth factor on fibroproliferation and effect of cytokine antagonists", Immunopharmacology, 1994, 28(3):259-270.
Extended European Search Report mailed Mar. 22, 2011 for European Patent Application No. 08841953.6 filed Oct. 23, 2008.

* cited by examiner

COMPOSITIONS AND METHODS FOR TREATING FIBROPROLIFERATIVE DISORDERS

REFERENCE TO RELATED APPLICATIONS

This application claims the benefit of the filing date of U.S. provisional patent application No. 60/983,026 filed 26 Oct. 2007, the entirety of which is hereby incorporated by reference.

TECHNICAL FIELD

This invention relates to fibroproliferative disorders. In particular, this invention relates to compositions and methods for treating fibroproliferative disorders.

BACKGROUND

Tissue damage may result from physical injury, infection, exposure to toxins, auto-immune processes and other causes. The physiological process of normal wound repair after tissue injury involves inflammation, the recruitment, activation and proliferation of fibroblasts and the secretion of extracellular matrix. This response ordinarily culminates in healing and termination of the proliferative and secretory processes. However, in clinically diverse conditions, the fibroproliferative response becomes itself detrimental and produces an abnormal accumulation of fibrocellular scar tissue that further compromises the normal architecture and function of the affected tissue and, in time, becomes the main cause for morbidity and mortality in these conditions.

As shown schematically in FIG. 1, injuries to normal tissues result in production of reactive oxidative species (ROS) and the release of cytokines, including TNF-α, PDGF, ET-1, bFGF, VEGF, TGF-β1 and chemokines CCL2 and CCL7. Mononuclear cells (monocytes/macrophages and neutrophils), T-lymphocytes and fibroblasts are recruited to the injury site. In response to released cytokines, these cells become activated and are a source for pro-fibrotic cytokines, namely TGF-β1 and CTGF. "Activated" fibroblasts transdifferentiate into myofibroblasts which are collagen type I producing cells. The final result is aberrant tissue remodeling, fibrosis and permanent scarring.

Pathological fibrosis can occur in almost any organ or tissue in the body. Examples include, but are not limited to:
1) All forms of pulmonary fibrosis from coal miners' Black Lung Disease to the treatment-induced varieties occurring in cancer patients and premature babies. Typically fibrocellular scar tissue severely reduces lung diffusion capacity, vital capacity and progresses relentlessly to respiratory failure and death.
2) All forms of liver fibrosis and cirrhosis.
3) All forms of vascular fibrosis such as atherosclerosis and diabetic complications.
4) All forms of renal fibrosis.
5) All forms of interventional therapy triggered fibrosis such as restenosis of blood vessels after balloon angioplasties and atherectomies.

These fibroses are the cause of much suffering, disability and death in millions of patients across the world.

In recent years, due to growing understanding of biochemical and molecular events underlying the progression of fibrosis in whatever organ is affected, reasonable scientific strategies have been generated and, as a result, several experimental drugs for treatment or prophylaxis of fibrosis are in clinical trials and there is considerable optimism that additional new therapies will emerge in the years ahead.

Typically, treatment of fibroproliferative disorders comprises removal of the underlying cause (e.g., toxin or infectious agent), suppression of inflammation (using, e.g., corticosteroids and immunosuppressive agents such cyclophosphamide and azathioprine), inhibition of fibroblast-like cell proliferation (using colchicines, penicillamine), down-regulation of cytokine machinery (using anti-TGF-beta antibodies, endothelin receptor inhibitors, interferons, pirfenidone and others), promotion of matrix degradation (using inhibitors of matrix metalloproteinases), or promotion of fibroblast apoptosis. Despite recent progress, many of these strategies are still in the experimental stage, and existing therapies are largely aimed at suppressing inflammation rather than addressing the underlying biochemical processes. Thus, there remains a need for more effective methods for treating fibroproliferative disorders.

Studies have demonstrated that pentoxifylline (PTX) is capable of positively effecting fibroproliferative disorders in a multi-potent manner. First, as a pan-phosphodiesterase inhibitor, pentoxifylline improves microcirculation and tissue oxygenation of the fibrotic tissue [1-3]; second, pentoxifylline alters the biochemical and physical properties of platelets thus decreasing platelet aggregation in fibrotic tissues [4]; third, pentoxifylline exerts significant anti-cytokine and anti-inflammatory activity, as it is principally capable of inhibiting the pro-inflammatory actions of interleukin-1 (IL-1) and tumor necrosis factor-α (TNF-α) on neutrophil function and cytokine production by monocytic cells [5]. Finally, pentoxifylline has shown direct inhibition of proliferation and collagen synthesis of human fibroblasts derived from normal and keloid skin and from hypertrophic scars [6]. Other phosphodiesterase inhibitors have some or all of the effects of pentoxifylline [19, 20].

Use of pentoxifylline as the sole agent in the treatment of liver and other fibrosis is claimed in U.S. Pat. No. 5,985,592 to Peterson entitled Uses for Pentoxifylline or Functional Derivatives/Metabolites Thereof. It is well known that fibroproliferative disorders are characterized by an accumulation of immunomodulatory cells (macrophages and neutrophils), parenchymal injury, and fibrosis [7]. Those cells in the affected tissue release exaggerated amounts of highly reactive oxygen radicals (oxidants), which mediate the parenchymal cell damage that typifies fibroproliferative disorders [21-24]. This oxidant burden is even more consequential due to a deficiency of glutathione, the major component of the antioxidant defense systems that normally protect against oxidant induced injury [8, 9].

In addition, low glutathione levels seem to play a major role in the exaggerated fibroblast proliferation seen in fibrosis [10]. Therefore, a rational therapeutic strategy for fibroproliferative disorders is to augment glutathione levels that would serve as protective screen to counterbalance toxic oxygen radicals.

For many years, N-acetyl-L-cysteine (NAC), a glutathione precursor, has been widely used as a mucolytic drug in pulmonary medicine [25]. The antioxidant potential of N-acetyl-L-cysteine has been established in vitro and in vivo. In vitro, the antioxidant capacity of N-acetyl-L-cysteine is directly related to the inactivation of electrophilic groups of free radicals [11, 12]. In vivo, N-acetyl-L-cysteine exerts its function as an antioxidant via its main metabolite, cysteine, the major precursor in the biosynthesis of glutathione [13]. In this respect, in paracetamol poisoning, oral N-acetyl-L-cysteine is able to replenish liver glutathione pools and to prevent drug-induced hepatotoxicity [14, 15]. In patients with lung tumours, oral treatment with N-acetyl-L-cysteine leads to an increase of glutathione levels in venous plasma and bronchoalveolar lavage fluid [16].

Oral N-acetyl-L-cysteine therapy in pulmonary fibrosis patients not only increased lung glutathione levels, but it did so with no short-term adverse effects. The therapy was safe, as judged by all routine clinical and bronchoscopic parameters evaluated [10].

SUMMARY OF THE INVENTION

A method of treating fibroproliferative disorders and delaying disease progression associated therewith in a mammal is provided. The method comprises administering a composition comprising a phosphodiesterase inhibitor in combination with an anti-oxidant which is a precursor of glutathione. In one embodiment, the phosphodiesterase inhibitor is pentoxifylline and the anti-oxidant is N-acetyl-L-cysteine. In another embodiment, the composition comprises derivatives or metabolites of either or both of the phosphodiesterase inhibitor and the anti-oxidant.

In one embodiment, the method comprises administering a daily dose of pentoxifylline in the range of 10 mg/kg and a daily dose of N-acetyl-L-cysteine in the range of 20 mg/kg. In other embodiments, the daily dose of pentoxifylline may be in the range of 200 mg to 1200 mg, and the daily dose of N-acetyl-L-cysteine may be in the range of 200 mg to 1800 mg. In some embodiments, the ratio of pentoxifylline to N-acetyl-L-cysteine may be in the range of 2:1 to 1:2. In one embodiment, the ratio of pentoxifylline to N-acetyl-L-cysteine is 1:2. A pharmacologically effective dose of the phosphodiesterase inhibitor and a pharmacologically effective dose of the anti-oxidant are effective in combination to treat a fibroproliferative disorder. In some embodiments, the pharmacologically effective dose of the phosphodiesterase inhibitor and the pharmacologically effective dose of the anti-oxidant are reduced respectively to a level below a pharmacologically effective dose of the phosphodiesterase inhibitor when the phosphodiesterase inhibitor is administered individually, and below a pharmacologically effective dose of the anti-oxidant when the anti-oxidant is administered individually.

A composition comprising a pharmacologically effective dose of a phosphodiesterase inhibitor and a pharmacologically effective dose of an anti-oxidant which is a precursor of glutathione is also provided. In some embodiments of the invention, the phosphodiesterase inhibitor is pentoxifylline and the anti-oxidant is N-acetyl-L-cysteine. In other embodiments of the invention, the composition comprises derivatives or metabolites of either or both of the phosphodiesterase inhibitor and the anti-oxidant.

The composition may include the phosphodiesterase inhibitor and the anti-oxidant in a dosage unit form. In some embodiments, the dosage unit form may include in the range of 200 mg to 1200 mg pentoxifylline, and in the range of 200 mg to 1800 mg of N-acetyl-L-cysteine. In some embodiments, the ratio of pentoxifylline to N-acetyl-L-cysteine in the dosage form may be in the range of 2:1 to 1:2. In one embodiment, the ratio of pentoxifylline to N-acetyl-L-cysteine in the dosage form is 1:2. In some embodiments, the dosage form is suitable to administer a daily dosage of pentoxifylline in the range of 10 mg/kg, and to administer a daily dosage of N-acetyl-L-cysteine in the range of 20 mg/kg.

BRIEF DESCRIPTION OF DRAWINGS

In drawings which show non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The present invention relates to methods and compositions for treating fibroproliferative disorders in mammals. In one embodiment, the method comprises administering to a mammal in need of such treatment an effective amount of a composition comprising pentoxifylline and N-acetyl-L-cysteine.

The terms "treat" and "treatment" are used broadly to denote therapeutic and prophylactic interventions that favorably alter a pathological state. Treatments include procedures that moderate or reverse the progression of, reduce the severity of, prevent, or cure a disease. As used herein, the term "fibroproliferative" includes all forms of pulmonary fibrosis (idiopathic, occupational and environmental, auto-immune, scleroderma, sarcoidosis, drug- and radiation-induced, genetic/familial fibrosis); all forms of liver fibrosis and cirrhosis; all forms of kidney fibrosis, all forms of uterine fibrosis; all forms of vascular fibrosis such as atherosclerosis and diabetic complications; all forms of interventional therapy triggered fibrosis such as restenosis of blood vessels after balloon angioplasties and atherectomies.

Preferred active agents for use in the present invention include pentoxifylline (or a pharmaceutically acceptable derivative or metabolite thereof, for example those described by Fantin et al. (2006) [28]). However, other phosphodiesterase inhibitors may also be used. Examples of such compounds are sildenafil, vardenafil, and tadalafil [29]. While the use of N-acetyl-L-cysteine is also preferred, other precursor compounds that replenish glutathione concentration in bronchio-alveolar lavage can be used. Pharmaceutically acceptable derivatives or metabolites of N-acetyl-L-cysteine may also be used.

Figure 1:
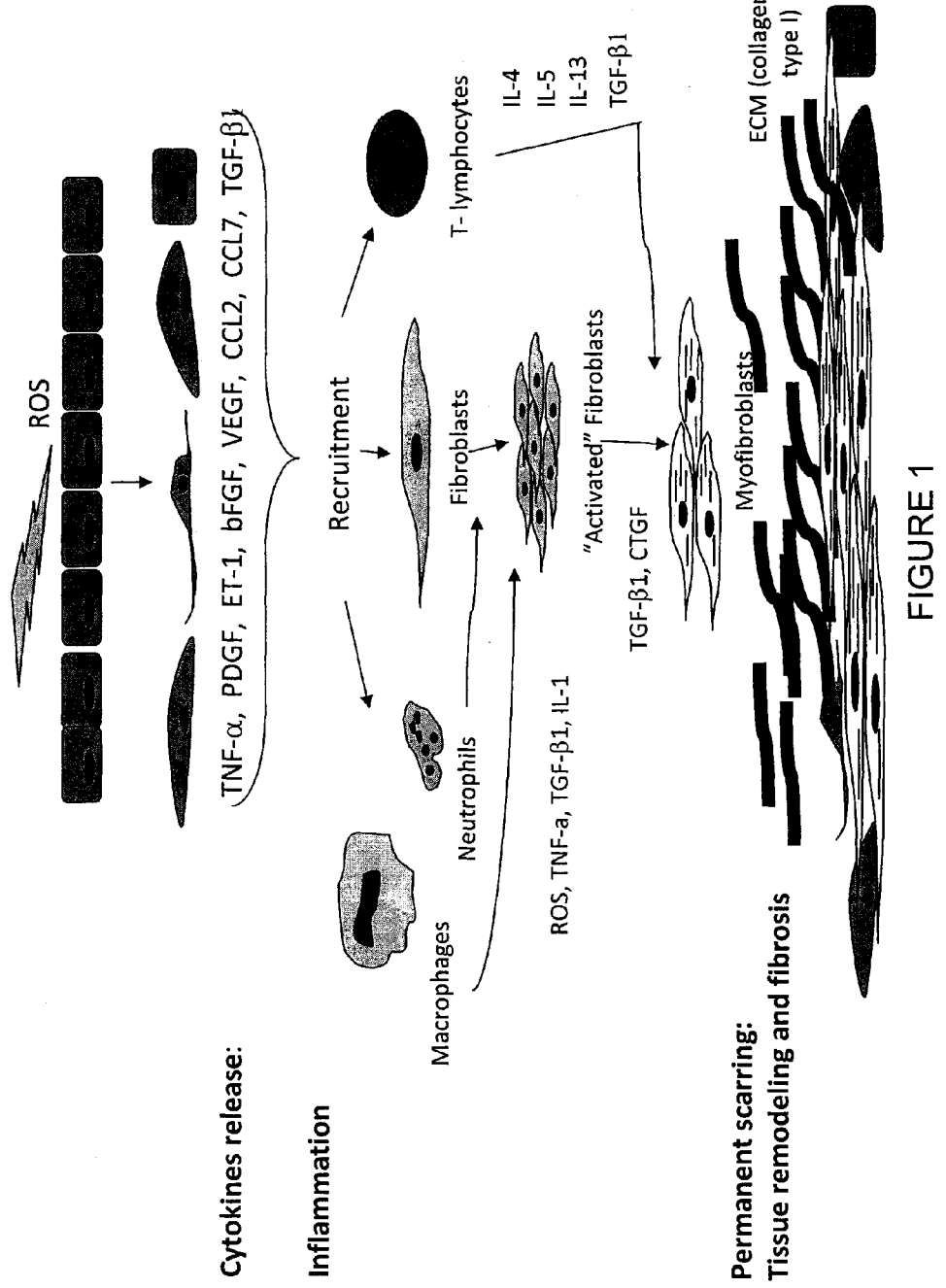
FIG. 1 is a schematic diagram illustrating the typical physiological progression of a fibroproliferative disorder.
Figure 2:
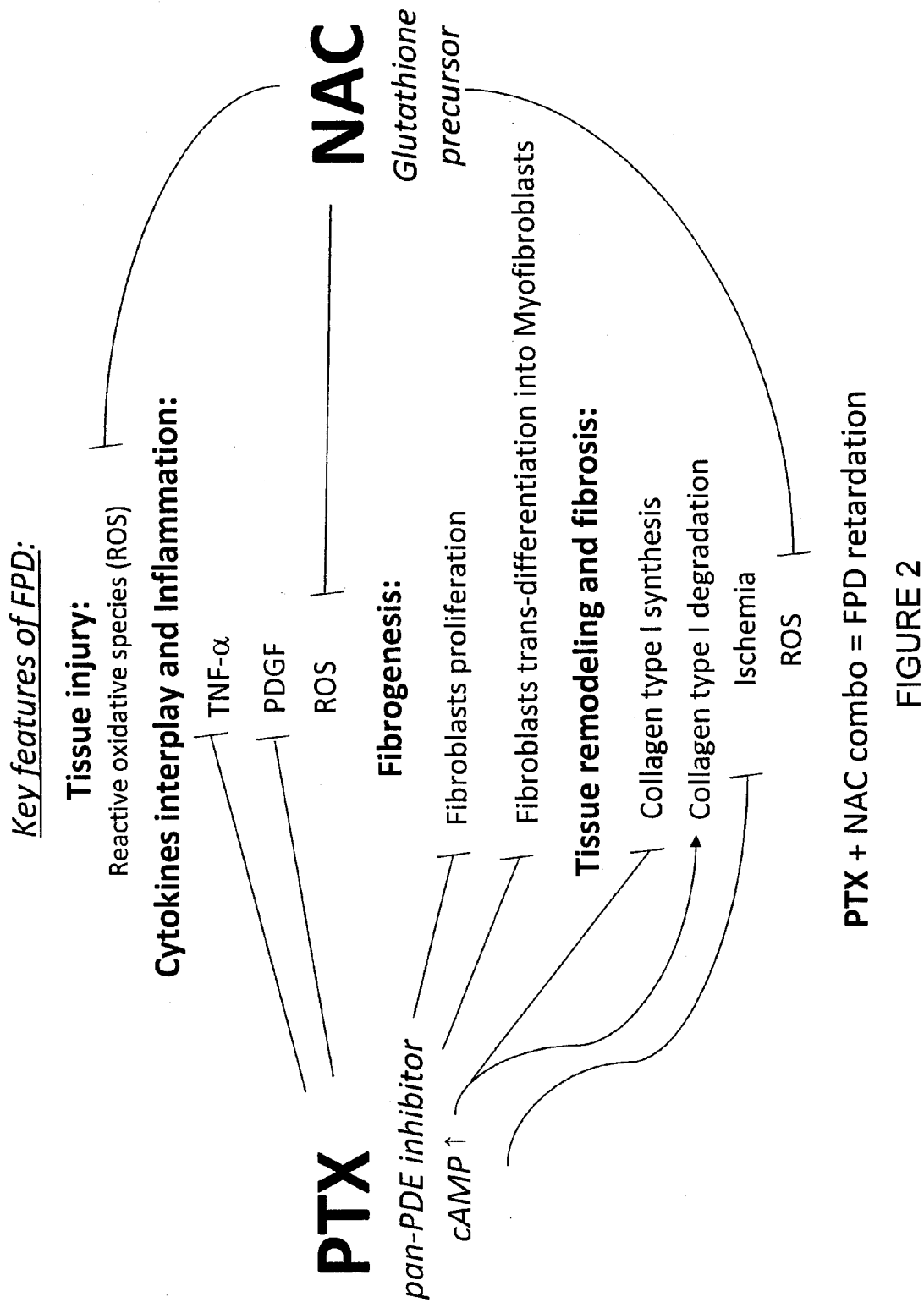
FIG. 2 is a schematic diagram illustrating the scientific rationale for using pentoxifylline and N-acetyl-L-cysteine in combination to treat fibroproliferative disorders.

As shown schematically in FIG. 2, the combination of pentoxifylline and N-acetyl-L-cysteine may be used in some embodiments of the present invention. Pentoxifylline, a known pan-phosphodiesterase inhibitor, works by increasing the intracellular level of cyclic adenosine monophosphate (cAMP), an important second messenger molecule in variety of cells. In several in vitro and in vivo systems, pentoxifylline has been shown to inhibit actions of some pro-fibrotic key cytokines including TNF-α [30, 31] and PDGF [32]. Moreover, pentoxifylline exerts strong inhibitory effects on both fibroblast proliferation and trans-differentiation of "activated" fibroblasts into myofibroblasts [33-36]. Myofibroblasts are cells that produce excessive extracellular matrix protein, collagen type I. In addition, pentoxifylline is capable of inhibiting collagen type I synthesis and promoting collagen type I degradation [35, 37-39]. These anti-fibrotic features of pentoxifylline as well as its known anti-ischemic property via vasodilation, coupled with low systemic toxicity, make pentoxifylline an attractive drug candidate for treatment of fibroproliferative disorders. However, other phosphodiesterase inhibitors such as sildenafil, vardenafil, and tadalafil may also be used in accordance with the present invention.

Still with reference to FIG. 2, N-acetyl-L-cysteine, a glutathione precursor and strong anti-oxidant, complements the anti-fibrotic effects of pentoxifylline by countering reactive oxygen radicals generated throughout the disease progression, thus helping to protect tissues from being further damaged. While reference is made to N-acetyl-L-cysteine, other precursors of glutathione (for example, NAC amide, cysteine esters, gammaglutamylcysteine and its ethyl ester, glutathione derivatives such as glutathione monoester, glutathione diester, lipoic acid and derivatives thereof) may also be used in accordance with the present invention. The final result of pentoxifylline and N-acetyl-L-cysteine combination treatment is retardation of fibroproliferative disorders.

The amount of active agents (e.g., pentoxifylline and N-acetyl-L-cysteine) administered can vary with the patient, the route of administration and the result sought. Optimum dosing regimens for particular patients can be readily determined by one skilled in the art. For example, the daily dose of pentoxifylline can be from about 200 mg to about 1200 mg combined with a daily dose of N-acetyl-L-cysteine from 200 mg to about 1800 mg. In one embodiment, the daily dose of pentoxifylline may be in the range of 10 milligrams per kilogram of body weight, and the daily dose of N-acetyl-L-cysteine may be in the range of 20 milligrams per kilogram of body weight. The ratio of pentoxifylline to N-acetyl-L-cysteine can range, for example, from about 2:1 to about 1:2.

The individual components of the composition can be administered separately at different times during the course of therapy or concurrently in divided or single combination forms.

In accordance with the present invention, the active agents (which may be, for example, pentoxifylline and N-acetyl-L-cysteine) can be administered in any convenient manner, such as orally, by inhalation intranasally, sublingually, rectally, vaginally, parenterally (including subcutaneously, intrathecally, intramuscularly or intravenously), cutaneously, or transdermally.

The active agents of the invention can be administered in the form of a pharmaceutical composition or compositions that contain one or both in an admixture with a pharmaceutical carrier. The composition may be formulated for topical or systemic administration. The pharmaceutical composition can be in dosage unit form such as tablet, capsule, sprinkle capsule, pill, granule, powder, syrup, suspension, emulsion, solution, gel including hydrogel, paste, ointment, cream, lotion, plaster, drench, suppository, enema, implant, spray or aerosol, suppository, injection or the like. Sustained released formulations can also be used. The composition can also be present in a transdermal delivery system, which may be, by way of example, a skin patch. A large variety of delivery vehicles for administering the composition are contemplated as within the scope of the present invention when containing therapeutic amounts of PDE inhibitor (for example, pentoxifylline) and antioxidant (for example, NAC). Suitable delivery vehicles include, but are not limited to, microcapsules or microspheres; liposomes and other lipid-based release systems; absorbable and/or biodegradable mechanical barriers, polymeric or gel-like materials.

In some embodiments, the dosage form may provide a dosage of between 200 to 1200 mg of pentoxifylline, and a dosage of between 200 mg and 1800 mg of N-acetyl-L-cysteine. The ratio of pentoxifylline to N-acetyl-L-cysteine in the dosage form may be in the range of 2:1 to 1:2. The dosage form may also be formulated to provide a daily dosage of pentoxifylline in the range of 10 milligrams per kilogram of body weight, and a daily dosage of N-acetyl-L-cysteine in the range of 20 milligrams per kilogram of body weight.

The pharmaceutical compositions may be formulated according to conventional pharmaceutical practice. Sustained release formulations can also be used. Each compound of the combination may be formulated in a variety of ways that are known in the art. For example, the first agent (PDE inhibitor) and the second agent (anti-oxidant) may be formulated together or separately. Desirably, the two components are formulated together for simultaneous administration. Such co-formulated compositions can include the two agents formulated together in the same pills, capsule, liquid, etc. The individually or separately formulated agents can be packaged together as a co-packaged product. Non-limiting examples include two pills, a pill and a powder, a suppository and a liquid in a vial, two topical creams, etc.

In accordance with the invention, the composition of pentoxifylline and N-acetyl-L-cysteine (including sustained release preparations) is an effective treatment for fibroproliferative disorders and provides an effective means of delaying disease progression associated with fibrosis. The composition can be more effective than, for example, pentoxifylline or N-acetyl-L-cysteine treatment alone and with fewer side effects. Lower doses of both types of medication can be used in the compound treatment, thereby further reducing the overall side effect burden. It is a particular advantage that, because of synergistic and superadditive effect on administration, the amounts of pentoxifylline and N-acetyl-L-cysteine which are to be administered can be reduced to those amounts which, on administration alone, show only minimal pharmacological side effects (i.e. the side effects which are elicited by high doses of these medicaments can be avoided or diminished). This is of great importance because it is known that N-acetyl-L-cysteine can, in the customary doses, elicit undesired side effects such as nausea, vomiting, headache, dry mouth, dizziness, or abdominal pain [17]. Moreover, pentoxifylline may show undesired side effects in the forms of malaise, flushing, dizziness/light-headedness, headache, nausea, vomiting, abdominal discomfort, bloating, diarrhea, dyspepsia [1, 18]. By means of the methods and compositions according to the invention it is now possible to reduce the dose of N-acetyl-L-cysteine necessary for mammals, including humans, as well as the amount of pentoxifylline, so that there is an even greater improvement in the general toxicological tolerability.

EXAMPLE 1.0

In Vivo Investigations in a Mouse Model

Methods

The composition including pentoxifylline (PTX) and N-acetyl-cysteine (NAC) was assessed in vivo in a mouse model using an experimental design in which a pulmonary fibrosis was generated using bleomycin injury of lung. Bleomycin (BLM) is an effective antineoplastic drug that binds to and damages DNA of tumour cells. However, administration of BLM may result in lung inflammation that can progress to fibrosis. This side effect is due mostly to augmented concentration of reactive oxygen species, decrease in nicotinamide adenine dinucleotide (NAD) and adenosine triphosphate (ATP), and overproduction of mature collagen fibrils. Because BLM-induced lung fibrosis is easily reproduced in different species of mammals, experimental models using the drug have been adopted with the goal of investigating the efficacy of the current invention [45].

From the literature, both N-acetyl cysteine (NAC) and pentoxifylline (PTX) individually have been shown to have efficacy in the bleomycin-induced lung injury animal model [40-44]. In this example, the effects of PTX and NAC in combination were studied in comparison to PTX and NAC individually. A comparison between the efficacy of the PTX/NAC combination vs. the combination of PTX and Vitamin E (another antioxidant) was also included in some experiments. The test substances were administered as shown in Table 1.

TABLE 1

Experimental Design of Bleomyin-Induced Pulmonary Fibrosis Mouse Model Study

| Group No. | Treatment | No. of animals | Test article (volume/dose); route of administration |
|---|---|---|---|
| I | Vehicle (negative) control | 5-20 | Saline (50 µl); IT Saline (100 µl); IP |
| II | BLM (positive) control | 5-20 | BLM (50 µl/0.06 U); IT Saline (100 µl); IP |
| III | BLM + PTX | 5-20 | BLM (50 µl/0.06 U); IT PTX (100 µl/10 mg/kg); IP |
| IV | BLM + NAC | 5-20 | BLM (50 µl/0.06 U); IT NAC (100 µl/20 mg/kg); IP |
| V | BLM + PTX/NAC combination | 5-20 | BLM (50 µl/0.06 U); IT PTX (50 µl/10 mg/kg); IP and NAC (50 µl/20 mg/kg); IP |
| VI | BLM + PTX/Vitamin E combination | 5 | BLM (50 µl/0.06 U); IT PTX (50 µl/10 mg/kg); IP and Vitamin E (50 µl/1.5 mg); IP |

Abbreviations: IP, Intraperitoneal; IT, Intratracheal; NAC, N-acetylcysteine; No., Number; PTX, Pentoxifylline; BLM, Bleomycin Mice (under anesthesia) received a single intratracheal dose of either saline (control) or bleomycin (BLM). The mice were administered intraperitoneal (IP) doses of saline, PTX, NAC, or Vitamin E and combinations thereof, daily for 14 days. On the appropriate day, the mice were given surgically deep anesthesia, total blood was obtained by cardiac puncture, bronchoalveolar lavage fluid (BALF) was collected from the lungs for further analysis of TNF-α and total glutathione (GSH) levels. In addition, the lung weights were recorded, photographs of the lungs were taken and tissue samples processed either for biochemical analysis of hydroxyproline (immediately frozen on dry ice) or further morphological analysis (immersed in fixative solution of 10% neutral-buffered formalin).

Results

Figure 3:
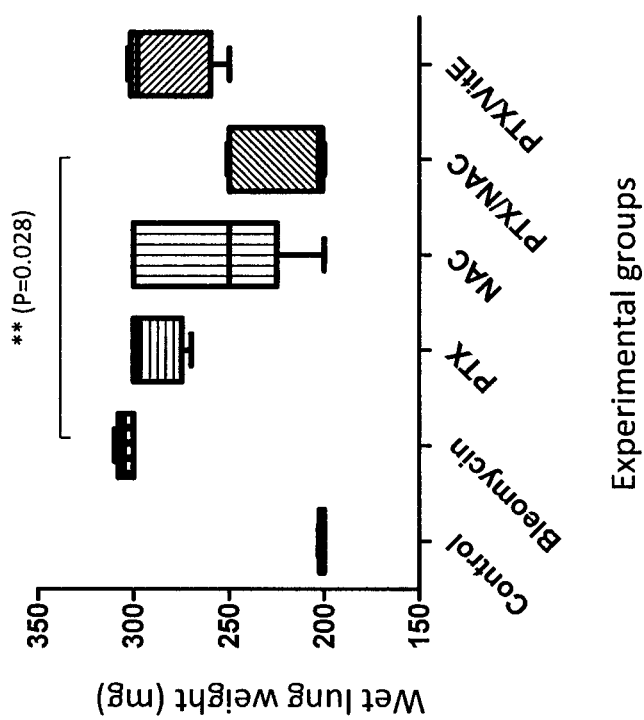
FIG. 3 illustrates the effect of pentoxifylline and N-acetylcysteine on wet lung weight. Lung weight (mg) in experimental groups, as indicated. Data are representative of 4 independent experiments, presented as mean±SD (n=5).

As anticipated, BLM (Group II) produced a significant increase in lung weight. In mice exposed to BLM and subsequently treated with PTX or NAC alone (Groups III and IV, respectively), lower lung weights were observed but statistical significance was not reached. However, when PTX and NAC were used in combination following bleomycin instillation (Group V), a statistically significant decrease in lung weight was observed (see FIG. 3—fourteen days treatment of the mice exposed to bleomycin resulted in lower lung weights but statistical significance was reached when PTX (pentoxifylline) and NAC (N-acetyl-cysteine) were used in combination).

Lungs from mice in control vehicle group (vehicle+vehicle) were histologically normal. Fourteen days after intratracheal bleomycin, lungs from mice in Group II (BLM+saline) showed marked peri-bronchiolar and interstitial infiltration with inflammatory cells, extensive cellular thickening of intra-alveolar septa, interstitial oedema, increases in interstitial cells with a fibroblastic appearance and in interstitial collagen deposition detected by the trichrome stain (i.e. fibrosis) (see FIG. 4; Panel B). These pulmonary lesions were markedly reduced in animals treated with the combination of pentoxifylline and NAC (Group V—bleomycin plus a combination of PTX and NAC—panel C). In Groups IV (BLM+NAC) and V (BLM+NAC and PTX), there was a marked anti-fibrotic effect seen, and although multifocal parenchymal lesions were still present in lungs, the organized foci were less frequent and smaller than those seen in untreated animals, showed less oedema and collagen deposition, and less septal widening and clusters of inflammatory cells (see FIG. 4; Panel C for Group V).

Figure 5:
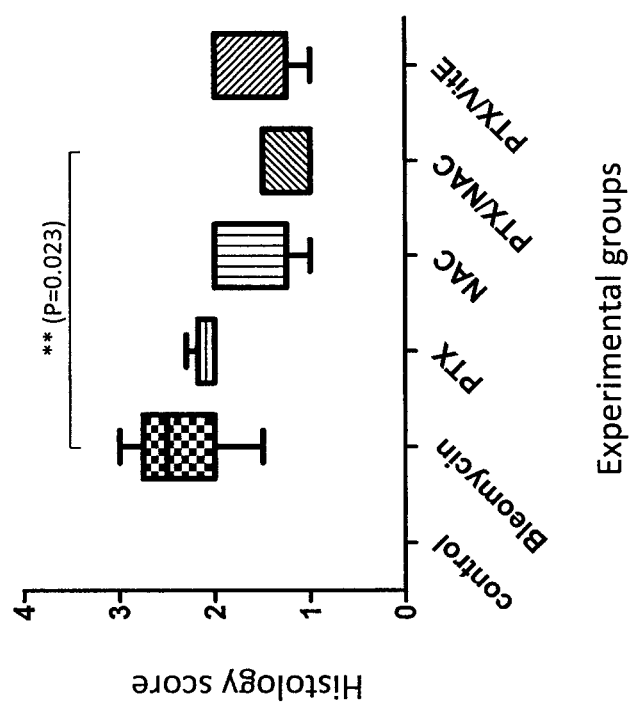
FIG. 5 illustrates the effect of pentoxifylline and N-acetylcysteine on histological lesions scores of the extent and severity of fibrosis in the experimental groups, as indicated. Data are representative of 5 independent experiments, presented as mean±SD (n=4).

The semi-quantitative score of the severity and extent of inflammation and fibrosis showed that most of indices were reduced in Group V (BLM+NAC and PTX), statistical significance was reached for scores related to severity and extension of fibrosis (see FIG. 5). The treatment combination of PTX and NAC had significant inhibitory effects on the severity and extent of BLM-initiated lung pathology. The PTX+NAC treatment was more effective than PTX or NAC alone and the combination of PTX+Vitamin E on the induced fibrosis in this animal model.

Figure 4:
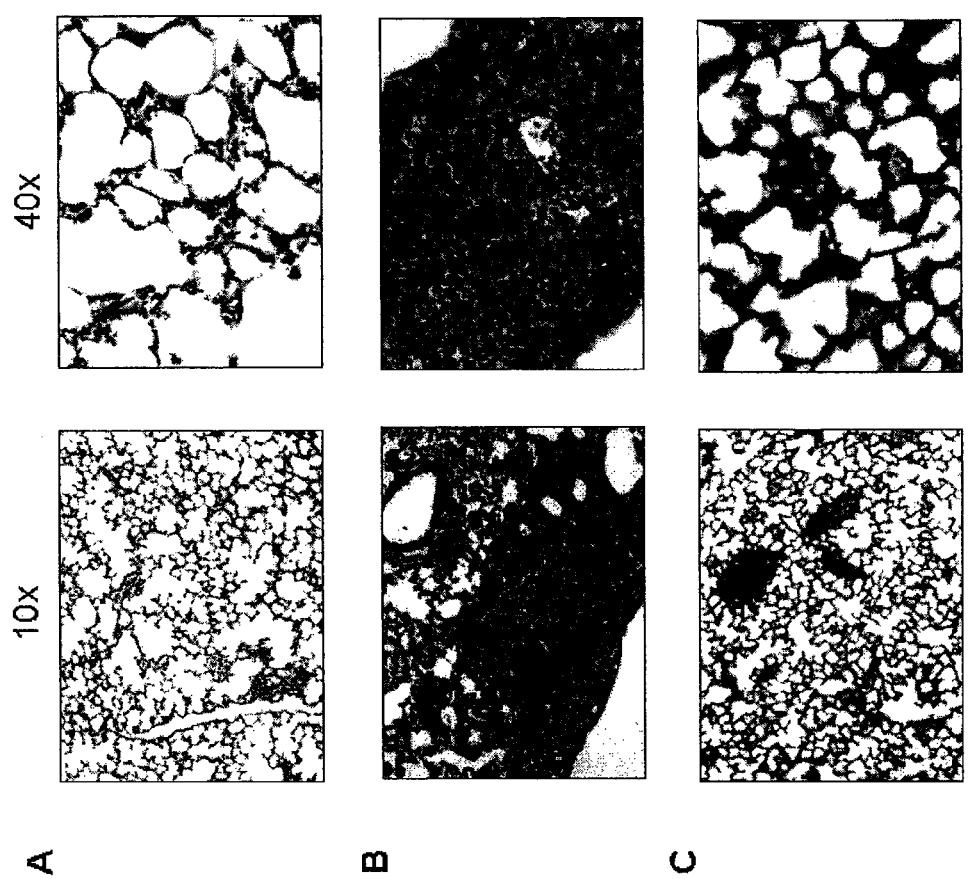
FIG. 4 illustrates representative photomicrographs of lung histopathology. Normal lung histology is shown in panel A (Group I-saline). Panel B shows results for Group II (bleomycin only) while Panel C shows results for Group V (bleomycin plus a combination of PTX and NAC). Collagen is stained with Masson trichrome (light blue color). Original ×10 and ×40 magnifications are shown.
Figure 6:
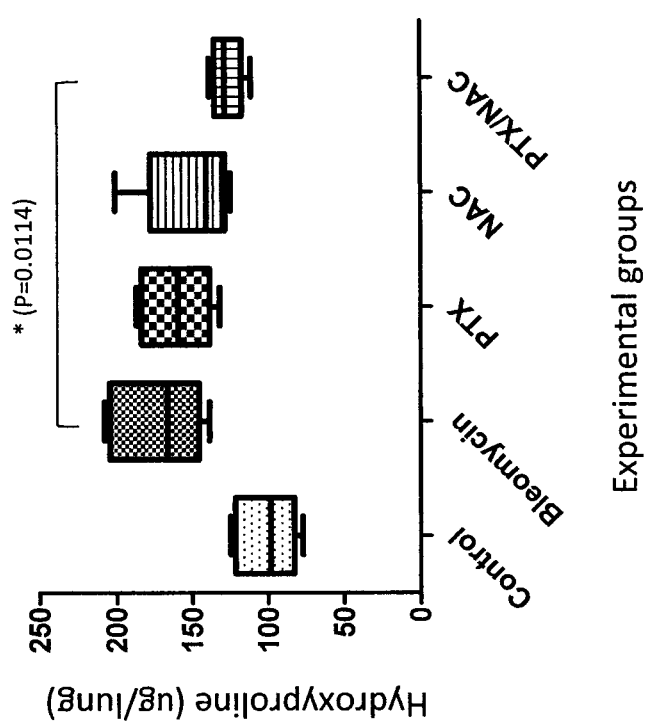
FIG. 6 illustrates the effect of pentoxifylline and N-acetylcysteine on a biochemical index of lung collagen accumulation—hydroxyproline—in the experimental groups, as indicated. Data are representative of 4 independent experiments, presented as mean±SD (n=5).

The extent of pulmonary fibrosis was also assessed biochemically. Lung hydroxyproline content was determined as an index of parenchymal collagen accumulation. FIG. 4 shows that intratracheal instillation of BLM induced a significant increase in total lung collagen compared with saline treatment. Administration of PTX and NAC combination therapy to bleomycin treated mice attenuated this increase by approximately 37% (see FIG. 6). Co-administration of PTX and NAC resulted in statistically significant reduction of the lung content of hydroxyproline.

Figure 7:
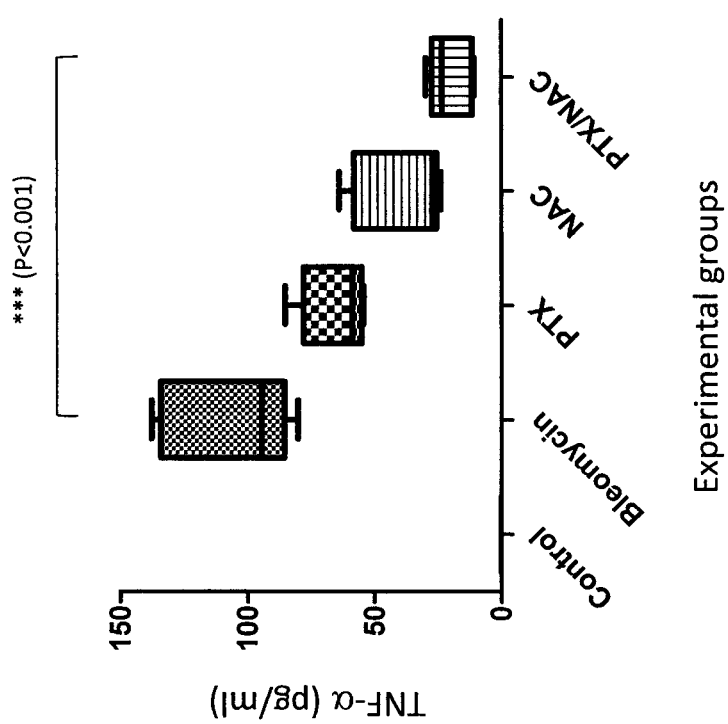
FIG. 7 shows results of TNF-α analysis (assayed by ELISA) in bronchoalveolar lavage fluid (BALF) in different experimental groups, as indicated. Difference of TNF-α at day 5 post bleomycin instillation is shown. Values are means±SD; 5 mice per group.
Figure 8:
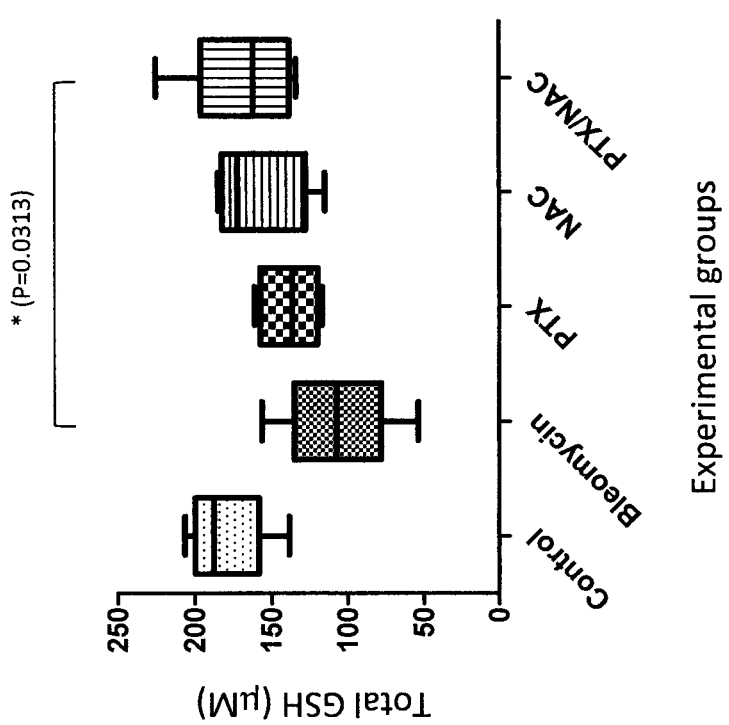
FIG. 8 illustrates total glutathione levels in bronchoalveolar lavage fluid (BALF) in different experimental groups, as indicated. Data are representative of 4 independent experiments, and presented as mean±SD (n=5).

To demonstrate that treatment with PTX and NAC alters cytokine release during the course of BLM-induced lung fibrosis, the inventors evaluated the release or secretion of proinflammatory cytokine TNF-α in the bronchoalveolar lavage fluid (BALF) using a commercially available ELISA kit. Treatment with either PTX or NAC significantly decreased BLM-induced increases in TNF-α level. Co-administration of PTX and NAC resulted in super-additive and synergistic effect (see FIG. 7). This beneficial effect of the combination can be explained by the reported ability of PTX to directly modulate production of TNF-α by inflammatory cells; and NAC's antioxidant ability to detoxify BLM-generated radicals before they damage lung tissue. In addition to a direct scavenging ability of BLM-generated oxygen radicals, NAC has protective effects through glutathione synthesis as a known precursor of glutathione (GSH). The inventors' data indicates that GSH is decreased in the BLM group, and that GSH levels can indeed be supplemented by daily administration of NAC (see FIG. 8). Therefore, the super-additive therapeutic effect observed with the combination therapy of PTX plus GSH can be also attributed to the daily supplementation of GSH, major lung anti-oxidant, in the alveolar space, thus helping to attenuate the BLM-induced lung injury.

Moreover, the inventors found no deaths or abnormal reactions with a daily co-administration of PTX and NAC during the experiments. The in vivo investigation of the combination therapy in a mouse model demonstrates that the therapy is likely a safe and effective method of treatment of pulmonary fibrosis in mammals.

As will be apparent to those skilled in the art in the light of the foregoing disclosure, many alterations and modifications are possible in the practice of this invention without departing from the spirit or scope thereof. It is therefore intended that the following appended claims and claims hereafter introduced are interpreted to include all such alterations and modifications as are within their true scope.

REFERENCES

1. Grigoleit, H. G. and G. Jacobi, *Microrheological effects of the vasoactive compound 3,7-dimethyl-1-(5-oxo-hexyl)-xanthine (pentoxifylline, BL 191)*. Vasa, 1977. 6(3): p. 274-8.
2. Weithmann, K. U., *The influence of pentoxifylline on interaction between blood vessel wall and platelets* IRCS Med. Sci., 1980(8): p. 293-294.
3. Aviado, D. M. and H. R. Dettelbach, *Pharmacology of pentoxifylline, a hemorheologic agent for the treatment of intermittent claudication*. Angiology, 1984. 35(7): p. 407-17.
4. Hammerschmidt, D. E., et al., *Pentoxifylline inhibits granulocyte and platelet function, including granulocyte priming by platelet activating factor*. J Lab Clin Med, 1988. 112(2): p. 254-63.
5. Balazs, C. and E. Kiss, *Immunological aspects of the effect of pentoxifylline (Trental) (a brief review)*. Acta Microbiol Immunol Hung, 1994. 41(2): p. 121-6.
6. Chang C. C., W. Y. C., Chiu H. C., Liu Y. L., and Lu Y. C., *Pentoxifylline inhibits the proliferation of human fibroblasts derived from normal, hypertrophic scar and keloid skin and their mitochondrial activity and collagen synthesis* European Journal of Dermatology, 1991. 1(3): p. 214-220
7. Wynn, T. A., *Common and unique mechanisms regulate fibrosis in various fibroproliferative diseases*. J Clin Invest, 2007. 117(3): p. 524-9.
8. Cantin, A. M., et al., *Oxidant-mediated epithelial cell injury in idiopathic pulmonary fibrosis*. J Clin Invest, 1987. 79(6): p. 1665-73.
9. Cantin, A. M., et al., *Normal alveolar epithelial lining fluid contains high levels of glutathione*. J Appl Physiol, 1987. 63(1): p. 152-7.
10. Meyer, A., R. Buhl, and H. Magnussen, *The effect of oral N-acetylcysteine on lung glutathione levels in idiopathic pulmonary fibrosis*. Eur Respir J, 1994. 7(3): p. 431-6.
11. Holdiness, M. R., *Clinical pharmacokinetics of N-acetylcysteine*. Clin Pharmacokinet, 1991. 20(2): p. 123-34.
12. Aruoma, O. I., et al., *The antioxidant action of N-acetylcysteine: its reaction with hydrogen peroxide, hydroxyl radical, superoxide, and hypochlorous acid*. Free Radic Biol Med, 1989. 6(6): p. 593-7.
13. Meister, A., *Glutathione metabolism and its selective modification*. J Biol Chem, 1988. 263(33): p. 17205-8.
14. Smilkstein, M. J., et al., *Efficacy of oral N-acetylcysteine in the treatment of acetaminophen overdose. Analysis of the national multicenter study* (1976 to 1985). N Engl J Med, 1988. 319(24): p. 1557-62.
15. Keays, R., et al., *Intravenous acetylcysteine in paracetamol induced fulminant hepatic failure: a prospective controlled trial*. Bmj, 1991. 303(6809): p. 1026-9.
16. Bridgeman, M. M., et al., *Cysteine and glutathione concentrations in plasma and bronchoalveolar lavage fluid after treatment with N-acetylcysteine*. Thorax, 1991. 46(1): p. 39-42.
17. Tattersall, A. B., K. M. Bridgman, and A. Huitson, *Acetylcysteine (Fabrol) in chronic bronchitis—a study in general practice*. J Int Med Res, 1983. 11(5): p. 279-84.
18. Muller, R. and F. Lehrach, *Haemorheology and cerebrovascular disease: multifunctional approach with pentoxifylline*. Curr Med Res Opin, 1981. 7(4): p. 253-63.
19. Valente, E. G., D. Vernet, et al. (2003). *L-arginine and phosphodiesterase (PDE) inhibitors counteract fibrosis in the Peyronie's fibrotic plaque and related fibroblast cultures*. Nitric Oxide 9(4): 229-44.
20. Kohyama, T., X. Liu, et al. (2002). *PDE4 inhibitors attenuate fibroblast chemotaxis and contraction of native collagen gels*. Am J Respir Cell Mol Biol 26(6): 694-701.
21. Moriyama, T., N. Kawada, et al. (2000). *Oxidative stress in tubulointerstitial injury: therapeutic potential of antioxidants towards interstitial fibrosis*. Nephrol Dial Transplant 15 Suppl 6: 47-9.
22. Aboutwerat, A., P. W. Pemberton, et al. (2003). *Oxidant stress is a significant feature of primary biliary cirrhosis*. Biochim Biophys Acta 1637(2): 142-50.
23. Rahman, I., S. K. Biswas, et al. (2006). *Oxidant and antioxidant balance in the airways and airway diseases*. Eur J Pharmacol 533(1-3): 222-39.
24. Kawada, N. and K. Otogawa (2007). *Role of oxidative stress and Kupffer cells in hepatic fibrosis*. J Gastroenterol Hepatol 22 Suppl 1: S85-6.
25. Sadowska, A. M., Y. K. B. Manuel, et al. (2007). *Antioxidant and anti-inflammatory efficacy of NAC in the treatment of COPD: discordant in vitro and in vivo dose-effects: a review*. Pulm Pharmacol Ther 20(1): 9-22.
26. Amores-Sanchez, M. I. and M. A. Medina (1999). *Glutamine, as a precursor of glutathione, and oxidative stress*. Mol Genet Metab 67(2): 100-5.
27. Chol, M., N. Nevo, et al. (2004). *Glutathione precursors replenish decreased glutathione pool in cystinotic cell lines*. Biochem Biophys Res Commun 324(1): 231-5.
28. Fantin, M., L. Quintieri, et al. (2006). *Pentoxifylline and its major oxidative metabolites exhibit different pharmacological properties*. Eur J Pharmacol 535(1-3): 301-9.
29. Kovanecz, I., A. Rambhatla, et al. (2007). *Chronic daily tadalafil prevents the corporal fibrosis and veno-occlusive dysfunction that occurs after cavernosal nerve resection*. BJU Int.

30. Navarro, J. F., C. Mora, et al. (1999). *Effects of pentoxifylline on the haematologic status in anaemic patients with advanced renal failure.* Scand J Urol Nephrol 33(2): 121-5.
31. Chen, Y. M., Y. Y. Ng, et al. (2004). *Pentoxifylline suppresses renal tumour necrosis factor-alpha and ameliorates experimental crescentic glomerulonephritis in rats.* Nephrol Dial Transplant 19(5): 1106-15.
32. Verma-Gandhu, M., M. R. Peterson, et al. (2007). *Effect of fetuin, a TGFbeta antagonist and pentoxifylline, a cytokine antagonist on hepatic stellate cell function and fibrotic parameters in fibrosis.* Eur J Pharmacol 572(2-3): 220-7.
33. Windmeier, C. and A. M. Gressner (1996). *Effect of pentoxifylline on the fibrogenic functions of cultured rat liver fat-storing cells and myofibroblasts.* Biochem Pharmacol 51(5): 577-84.
34. Desmouliere, A., G. Xu, et al. (1999). *Effect of pentoxifylline on early proliferation and phenotypic modulation of fibrogenic cells in two rat models of liver fibrosis and on cultured hepatic stellate cells.* J Hepatol 30(4): 621-31.
35. Strutz, F., M. Heeg, et al. (2000). *Effects of pentoxifylline, pentifylline and gamma-interferon on proliferation, differentiation, and matrix synthesis of human renal fibroblasts.* Nephrol Dial Transplant 15(10): 1535-46.
36. Rawlins, J. M., W. L. Lam, et al. (2006). *Pentoxifylline inhibits mature burn scar fibroblasts in culture.* Burns 32(1): 42-5.
37. Raetsch, C., J. D. Jia, et al. (2002). *Pentoxifylline down-regulates profibrogenic cytokines and procollagen I expression in rat secondary biliary fibrosis.* Gut 50(2): 241-7.
38. Fang, C. C., M. N. Lai, et al. (2003). *Effects of pentoxifylline on peritoneal fibroblasts and silica-induced peritoneal fibrosis.* Perit Dial Int 23(3): 228-36.
39. Xiong, L. J., J. F. Zhu, et al. (2003). *Effects of pentoxifylline on the hepatic content of TGF-beta1 and collagen in Schistosomiasis japonica mice with liver fibrosis.* World J Gastroenterol 9 (1): 152-4.
40. Cortijo, J., M. Cerda-Nicolas, et al. (2001). *Attenuation by oral N-acetylcysteine of bleomycin-induced lung injury in rats.* Eur Respir J 17(6): 1228-35.
41. Entzian, P., U. Zahringer, et al. (1998). *Comparative study on effects of pentoxifylline, prednisolone and colchicine in experimental alveolitis.* Int J Immunopharmacol 20(12): 723-35.
42. Hagiwara, S. I., Y. Ishii, et al. (2000). *Aerosolized administration of N-acetylcysteine attenuates lung fibrosis induced by bleomycin in mice.* Am J Respir Crit. Care Med 162(1): 225-31.
43. Mata, M., A. Ruiz, et al. (2003). *Oral N-acetylcysteine reduces bleomycin-induced lung damage and mucin Muc5ac expression in rats.* Eur Respir J 22(6): 900-5.
44. Serrano-Mollar, A., D. Closa, et al. (2003). *In vivo antioxidant treatment protects against bleomycin-induced lung damage in rats.* Br J Pharmacol 138(6): 1037-48.
45. Moore, B. B. and C. M. Hogaboam. (2008). *Animal models of pulmonary fibrosis.* Am J Physiol Lung Cell Mol Physiol 294(2): 152-160.

What is claimed is:

1. A method of treating pulmonary fibrosis in a mammal comprising administering a combination of a pharmacologically effective dose of pentoxifylline and a pharmacologically effective dose of N-acetyl-L-cysteine, wherein the daily dose of pentoxifylline is in the range of 200 mg to 1200 mg, and wherein the daily dose of N-acetyl-L-cysteine is in the range of 200 mg to 1800 mg.

2. A method according to claim 1 wherein the pentoxifylline and the N-acetyl-L-cysteine are administered separately.

3. A method according to claim 1 wherein the pentoxifylline and the N-acetyl-L-cysteine are administered concurrently.

4. A method according to claim 1 wherein the daily dose of pentoxifylline is 10 mg/kg, and wherein the daily dose of N-acetyl-L-cysteine is about 20 mg/kg.

5. A method according to claim 1 wherein the ratio of pentoxifylline to N-acetyl-L-cysteine is in the range of 2:1 to 1:2.

6. A method according to claim 5 wherein the ratio of pentoxifylline to N-acetyl-L-cysteine is 1:2.

7. A method according to claim 1 wherein both the pentoxifylline and the N-acetyl-L-cysteine are administered by any suitable means for oral, parenteral, rectal, cutaneous, nasal, vaginal, or inhalant use.

8. A method according to claim 1 wherein either or both of the pentoxifylline and the N-acetyl-L-cysteine are admixed with a pharmaceutical carrier before administration.

9. A method according to claim 1 wherein the pharmacologically effective dose of the pentoxifylline and the pharmacologically effective dose of the N-acetyl-L-cysteine are effective in combination to treat pulmonary fibrosis.

10. A method according to claim 9 wherein the pharmacologically effective dose of the pentoxifylline and the pharmacologically effective dose of the N-acetyl-L-cysteine are reduced respectively to a level below a pharmacologically effective dose of the pentoxifylline when the pentoxifylline is administered individually, and below a pharmacologically effective dose of the N-acetyl-L-cysteine when the N-acetyl-L-cysteine is administered individually.

11. A composition comprising a pharmacologically effective dose of pentoxifylline and a pharmacologically effective dose of N-acetyl-L-cysteine, wherein the dosage unit form comprises in the range of 200 mg to 1200 mg pentoxifylline, and in the range of 200 mg to 1800 mg of N-acetyl-L-cysteine.

12. A composition according to claim 11 wherein the pentoxifylline and the N-acetyl-L-cysteine are in dosage unit form.

13. A composition according to claim 12 wherein the composition is in the form of a tablet, capsule, granule, powder, syrup, suspension, emulsion, solution, gel, paste, ointment, cream, lotion, plaster, skin patch, drench, suppository, enema, injectable, implant, spray or aerosol.

14. A composition according to claim 12 wherein the ratio of pentoxifylline to N-acetyl-L-cysteine in the dosage form is in the range of 2:1 to 1:2.

15. A composition according to claim 14 wherein the ratio of pentoxifylline to N-acetyl-L-cysteine in the dosage form is 1:2.

16. A composition according to claim 12 wherein the dosage form is suitable to administer a daily dosage of pentoxifylline of about 10 mg/kg, and to administer a daily dosage of N-acetyl-L-cysteine of about 20 mg/kg.

17. A composition according to claim 11 further comprising a pharmaceutically acceptable carrier.

18. A composition according to claim 11 wherein the pharmacologically effective dose of pentoxifylline and the pharmacologically effective dose of N-acetyl-L-cysteine are effective in combination to treat pulmonary fibrosis.

* * * * *